of Search .................................... 568/902
United States Patent [19]

Cornils et al.

[11] 4,424,383

[45] Jan. 3, 1984

[54] PROCESS FOR PRODUCING ETHANOL AND N-PROPANOL FROM METHANOL

[75] Inventors: Boy Cornils, Dinslaken; Carl D. Frohning, Oberhausen; Gerhard Diekhaus, Oberhausen; Ernst Wiebus, Oberhausen; Helmut Bahrmann, Hünxe, all of Fed. Rep. of Germany

[73] Assignee: Ruhrchemie Aktiengesellschaft, Fed. Rep. of Germany

[21] Appl. No.: 320,008

[22] Filed: Nov. 10, 1981

[30] Foreign Application Priority Data

Nov. 11, 1980 [DE] Fed. Rep. of Germany ....... 3042434

[51] Int. Cl.³ ...................... C07C 31/08; C07C 29/00
[52] U.S. Cl. .................................................... 568/902
[58] Field of Search .......................................... 568/902

[56] References Cited

U.S. PATENT DOCUMENTS

| | | | |
|---|---|---|---|
| 3,248,432 | 4/1966 | Riley et al. | 568/902 |
| 3,387,043 | 6/1968 | Kuraishi et al. | 568/902 |
| 4,133,966 | 1/1979 | Pretzer et al. | 568/902 |
| 4,233,466 | 11/1980 | Fiato | 568/902 |
| 4,239,924 | 12/1980 | Pretzer et al. | 568/902 |
| 4,262,154 | 4/1981 | Gane et al. | 568/902 |
| 4,352,947 | 10/1982 | Habib et al. | 568/902 |

FOREIGN PATENT DOCUMENTS 2053915 2/1981 United Kingdom ............... 568/902

*Primary Examiner*—Joseph E. Evans
*Attorney, Agent, or Firm*—Jordan B. Bierman; Linda Bierman

[57] ABSTRACT

A method for the production of ethanol or propanol comprising the reaction of methanol with carbon monoxide and hydrogen in the presence of a catalyst. The catalyst contains a cobalt compound, a ruthenium compound, iodine or an iodide, and a bi-dentate organic phosphine or phosphite. The reaction is carried out at 150° to 250° C., 200 to 600 bars, and in the presence of 5 to 25% by weight of water, based on the methanol.

13 Claims, No Drawings

PROCESS FOR PRODUCING ETHANOL AND N-PROPANOL FROM METHANOL

This Application claims the benefit of the priority of German Application P 30 42 434.1, filed Nov. 11, 1980.

In recent years, the shortage of petroleum has focused attention on the creation of new methods for the production of chemical compounds which do not depend on this material. The present invention is directed to a method for the production of ethanol and/or n-propanol from methanol and synthesis gas. The method is called homologisation, and it enables the production of higher homologous alcohols to be produced from methanol by introducing, into the molecule, one or more methylene groups.

A suitable feed stock is synthesis gas or methanol produced therefrom. The gas can be obtained from coal or natural gas by various well known, reliable, and efficient processes.

The conversion of methanol into ethanol by reaction with hydrogen and carbon monoxide has been well known for a long time. An example of such a process is to be found in German Patent No. 867,849. The reaction is carried out in the presence of a water soluble cobalt catalyst at elevated temperatures and pressures, and proceeds according to the following equation.

$$CH_3OH + CO + 2H_2 \rightarrow C_2H_5OH + H_2O$$

In addition, there is some formation of higher alcohols in relatively small amounts. This proceeds in accordance with the equation:

$$CH_3OH + n(CO + 2H_2) \rightarrow CH_3(CH_2)_nOH + nH_2O$$

Originally, cobalt was used as the sole catalyst for this reaction. However, over a period of time, multi-component catalysts have become increasingly important. It is, of course, desirable to increase both the conversion rate and the selectivity in favor of ethanol. Various means have been described for doing so.

For example, U.S. Pat. No. 3,285,948 teaches a catalyst comprising cobalt with iodine or an iodine compound as a first promoter, and a ruthenium halide or osmium chloride as a second promoter.

Similarly, DOS No. 26 25 627 uses catalyst consisting of cobalt, a halide, and a tertiary phosphine. The halide is used as a promoter. The conversion is carried out in the presence of a hydrocarbon solvent.

In U.S. Pat. No. 4,133,966, the ethanol is obtained by using a catalyst which is cobalt acetyl acetonate, an organic compound of an element of Group VA of the Periodic Table of the Elements, a ruthenium compound, and an iodine compound.

The foregoing processes are intended to improve the selectivity of the reaction while maintaining good conversion. However, considerable improvement of their characteristics is extremely desirable. It will be understood that the undesired by-products of this reaction are not only produced in large quantities, but also constitute numerous different compounds. For example, in addition to the desired alcohols, by-products include methane, ethane, propane, ethers, methyl acetate, ethyl acetate, propyl acetate, acetaldehyde-dimethyl-acetal, acetaldehyde-methylethyl acetal, and acetaldehydediethyl acetal. To commercialize these processes, it is necessary to expend considerable sums of money in order to isolate the desired fractions from the numerous and varied impurities. Hydrogenation, saponification, and distillation are among the procedures used for purification of the mixtures which result from the carrying out of the reaction.

It has been suggested that the selectivity of the conversion be improved by the addition of a solvent. However, this results in a substantial reduction in conversion based upon reactor volume and time.

In general, the known processes will convert methanol to the higher alcohols either with satisfactory selectivity and low conversion, or high conversion and low selectivity.

Therefore, it is among the objects of the present invention to provide a method for the production of ethanol and n-propanol from methanol which will proceed with both high selectivity and good conversion.

It is also among the objects of this invention to provide a procedure for the production of these alcohols from methanol which will substantially reduce the number of by-products, so that the desired alcohols can be separated from the reaction mixture in a simple manner.

The reaction according to the present invention is carried out by converting methanol with carbon monoxide and hydrogen to ethanol and n-propanol at elevated pressures and temperatures. The catalyst used contains a cobalt compound, a ruthenium compound, iodine or an iodide, and a bi-dentate organic phosphine or phosphite. The reaction temperature is 150° to 250° C. and the pressure is 200 to 600 bars and there is 5 to 25% by weight of water present, based on the methanol.

The bi-dentate compounds of the present invention include those substances wherein the molecules contain two phosphorous atoms which simultaneously act as donors. Particularly suitable compounds falling within this class are those of the formula:

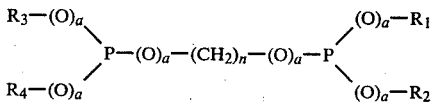

$R_1$, $R_2$, $R_3$, and $R_4$ are individually hydrogen, straight or branched chain alkyl radicals having 1 to 16 carbon atoms, or aryl radicals with 6 to 15 carbon atoms; a is 0 or 1, and n is an integer from 1 to 6. It is also contemplated that each member of the pairs of radicals $R_1$ and $R_2$, and $R_3$ and $R_4$, may be individually joined to the other to form a phosphorous containing heterocyclic ring.

Typical alkyl radicals which are useful in the present invention are methyl, ethyl, propyl, butyl, pentyl, i-propyl, i-hexadecyl, and neopentyl. Cycloalkyl radicals may advantageously be cyclohexyl and dicyclopentyl. Suitable aryl radicals include phenyl, tolyl, naphthyl, and phthalyl.

$R_1$ and $R_4$ may be joined to their respective phosphorous atoms by oxygen atoms. Typical of the bi-dentate compounds which are useful in the present invention are

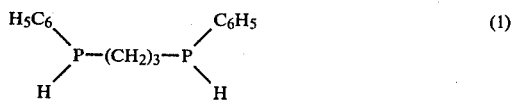

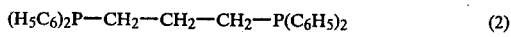

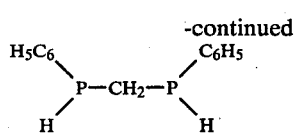

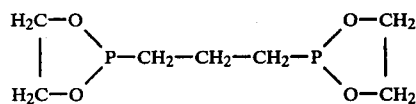

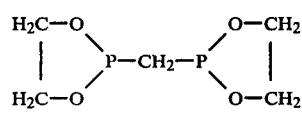

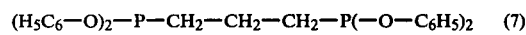

It has been found that 1,3-bis-(diphenylphosphino)-propane (Compound 2) and bis-(diphenylphosphino)-methane (Compound 4) are to be preferred.

It is believed that phosphorous compounds of the present invention form complexes with the cobalt and ruthenium compounds under the conditions of the reaction. Such compounds may also contain carbon monoxide and hydrogen and form a constituent of an effective catalyst system.

It has been found advantageous to add cobalt to the reaction mixture in the form of a salt such as cobalt 2-ethylhexanoate, cobalt acetylacetonate, cobalt halide, cobalt nitrate, or as an oxide or hydroxide. It is also possible to use metallic cobalt in finely divided form. The carbonate has been found to be particularly suitable for this reaction. It is important to note that the cobalt (or compounds thereof) reacts with carbon monoxide and hydrogen to form a cobalt carbonyl or cobalt hydrocarbonyl.

The ruthenium is added to the reaction mixture as a compound which is converted into carbonyl complexes under the reaction conditions. The ruthenium is advantageously added as ruthenium halide, ruthenium 2-ethylhexanoate, ruthenium acetylacetonate, or $(NH_4)_4[Ru_2OCl_{10}]$. The preferred compound is ruthenium chloride ($RuCl_3$).

The iodine is present either in molecular or ionic form. Alkali metal salts are useful as the iodides. In particular, cobalt iodide has been found useful and convenient.

The present catalyst system may be added to the reaction mixture in the form of its individual constituents. Thus, is is not necessary to preform the metal complex compounds. Moreover, the system can be used repeatedly.

If desired, the various catalysts and components thereof may be suspended or dissolved in a high boiling point solvent. Such compounds as diethylene glycol ether (Diglyme), tetraethylene glycol ether (Tetraglyme), neopentyl glycol (2,2-dimethyl-1,3-propanediol), ethylene glycol, or 2-ethylhexanol have been found suitable. Those solvents or suspending agents which are the organic by-products of the reaction and have a higher boiling point than the desired end products (ethanol and n-propanol) are particularly advantageous in this process.

Methanol which is the product of commercial plants and has a water content of 4 to 6% may be used as the starting material. Further purification of this material is usually unnecessary.

For best results, the original reaction mixture should contain 5 to 25% by weight of water, based on the amount of methanol present. This addition has been found to increase the conversion rate. Increased amounts of water have only a slight effect on the conversion, while smaller amounts have either a slight effect, or none at all. The water can be conveniently added with the methanol directly into the reactor.

The molar ratio of cobalt to methanol is 1:20 to 1:10,000; preferably 1:30 to 1:2,000. The cobalt and phosphine or phosphite are used in a molar ratio of 1:1 to 1:20; preferably 1:1 to 1:5. The atomic ratio of cobalt to ruthenium is 1:0.0005 to 1:0.5; preferably 1:0.05 to 1:0.1. Cobalt and iodine are used in a atomic ratio of 1:0.02 to 1:2; preferably 1:0.1 to 1:1. The foregoing ratios have been found to be advantageous in the carrying out of this reaction. However, they are not essential thereto.

For best results, the carbon monoxide/hydrogen mixture should contain no impurities (such as sulfur) which will affect the activity of the catalyst. Such impurities as carbon dioxide and/or nitrogen in amounts of up to 5% by volume, based on the total mixture, have been found to be not harmful.

The present process is suitable for both batch and continuous reactions. It has been found effective to carry out the conversion at 150° to 250° C., preferably 160° to 230° C. The pressure is from 200 to 600 bars, preferably 450 to 600 bars. The molar ratio of hydrogen to carbon monoxide in the synthesis gas is advantageously 1:1 to 10:1.

The following examples are intended to illustrate the invention, without being limitative thereof:

EXAMPLE 1

6.25 moles (200 g) of methanol, 1.1 moles (19.80 g) of water, 17 mmoles (2.02 g $CoCO_3$) of Co, 6.7 mmoles (1.00 g NaI) of iodide, 22.1 moles (9.11 g) of 1,3-bis-(diphenylphosphino)propane and 1 mmole (0.26 g $RuCl_3.3 H_2O$) of Ru are placed in a 1 liter steel autoclave. The autoclave is equipped with a stirrer, temperature measurement device, sample extraction pipe, and a gas holder serving to collect gaseous constituents. A pressure of 550 bars is then established with synthesis gas (CO: $H_2$=1:3), the contents are heated to 185° C., and the reaction is continued for 6 hours, while pumping in synthesis gas. After cooling the reaction mixture and releasing the pressure in the gas holder, an average sample, whose gas chromatographic composition and conversion and selectivity data are shown in Tables 1 and 2, is collected.

EXAMPLE 2

4.5 moles (144 g) of methanol, 0.8 moles (14.40 g) of water, 134 mmoles (15.95 g $CoCO_3$) of Co, 53 mmoles (7.95 g NaI) of iodide, 146 mmoles (60.15 g) of 1,3-bis-(diphenylphosphino)propane and 7.90 mmoles (3.15 g Ru-III-acetylacetonate) of Ru are placed in the steel autoclave of the apparatus of Example 1. A pressure of 280 bars is then established with synthesis gas (CO: $H_2$=1:3), the contents are heated to 185° C., and the reaction is continued for 3 hours while forcing in synthesis gas. A sample is taken as described in Example 1, and the gas chromatographic composition and conversion and selectivity data thereof are given in Tables 1 and 2.

EXAMPLE 3

The reaction mixture formed in Example 2 is freed from all volatile constituents by distillation, and the dry residue, in place of the catalyst system, is recycled to the reaction as described in Example 2 together with 4.5 moles (144.0 g) of methanol and 0.8 mole (14.4 g) of water. A pressure of 550 bars is then established with synthesis gas (CO: $H_2 = 1:3$), the contents are heated to 185° C., and the reaction is continued for 3 hours while forcing in synthesis gas.

The sample is taken as described in Example 1, and the gas chromatography composition and other data thereof are given in Tables 1 and 2.

EXAMPLE 4

The same conditions as specified in Example 1 are maintained but, instead of 1,3-bis-(diphenylphosphino)-propane, 22.1 mmoles (8.49 g) of bis-(diphenylphosphino)-methane are used. The reaction is carried out as described in Example 1 and the results set forth in Tables 1 and 2.

EXAMPLE 5

The reaction mixture of Example 4 is freed from all volatile constituents by distillation, and the dry residue is recycled in the reaction, as specified in Example 4, together with 6.25 moles (200.0 g) of methanol and 1.1 mole (19.80 g) of water. The same conditions as in Example 1 are maintained and the results are set forth in Tables 1 and 2.

EXAMPLE 6

9.375 moles (300.0 g) of methanol, 1.667 moles (30.0 g) of water, 25.50 mmoles (3.03 g $CoCO_3$) of Co, 10 mmoles (150 g NaI) of iodide, 1.50 mmoles (0.60 g Ru-III-acetylacetonate) of Ru and 28.10 mmoles (7.30 g) of 1,3-bis-(monophenylphosphino)propane are placed in the steel autoclave of the apparatus according to Example 1 and reacted further as described in Example 1. The results are set forth in Tables 1 and 2.

EXAMPLE 7

The same conditions as specified in Example 6 are maintained, but instead of 1,3-(bis-monophenylphosphino)-propane, 28.10 mmoles (6.30 g) of 1,3-bis-[1,3,2-dioxaphospholanyl-(2)]propane are used. The reaction is carried out as described in Example 1 and the results are set forth in Tables 1 and 2.

TABLE 1

| | GLC-Analysis (% by wt.) | | | | | | |
|---|---|---|---|---|---|---|---|
| | Examples | | | | | | |
| Components | 1 | 2 | 3 | 4 | 5 | 6 | 7 |
| Alkanes | 3,3 | 2,6 | 6,4 | 3,1 | — | 2,5 | 2,2 |
| Ethers | 3,6 | 0,8 | 2,3 | 2,6 | 0,8 | 2,1 | 2,9 |
| Esters | 1,7 | 0,5 | 2,2 | 1,2 | 0,8 | 1,3 | 1,5 |
| Acetals | — | — | — | 1,5 | 1,2 | 0,3 | 0,6 |
| Methanol | 47,7 | 59,5 | 27,7 | 56,0 | 70,7 | 64,0 | 57,6 |
| Ethanol | 40,7 | 29,6 | 53,5 | 31,2 | 24,3 | 27,6 | 32,3 |
| n-Propanol | 2,3 | 5,6 | 5,3 | 1,6 | 0,8 | 0,9 | 1,3 |
| Higher Alcohols | 0,7 | 0,3 | 0,7 | 1,9 | 0,5 | 0,6 | 1,1 |
| Last runnings | Spur | 1,1 | 1,9 | 0,9 | 0,9 | 0,7 | 0,5 |

TABLE 2

| | Examples | | | | | | |
|---|---|---|---|---|---|---|---|
| | 1 | 2 | 3 | 4 | 5 | 6 | 7 |
| Conversion referred to Methanol (in %) | 52,3 | 40,5 | 72,3 | 44,0 | 29,3 | 36,0 | 42,4 |
| Selectivity for Ethanol (in %) | 78,0 | 73,1 | 73,9 | 71,0 | 83,8 | 77,0 | 76,0 |
| Selectivity for Propanol (in %) | 4,0 | 13,8 | 7,4 | 8,0 | 2,8 | 3,0 | 3,0 |

While only a limited number of specific embodiments of the present invention have been expressly described, it is, nonetheless, to be broadly construed and not to be limited except by the character of the claims appended hereto.

What we claim is:

1. A method for the production of ethanol and n-propanol comprising reacting methanol with carbon monoxide and hydrogen in the presence of a catalyst containing a cobalt compound, a ruthenium compound, iodine or an iodide, and a bi-dentate organic phosphine or phosphite of the formula

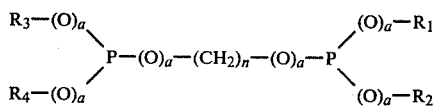

wherein $R_1$, $R_2$, $R_3$, and $R_4$ are individually hydrogen, alkyl radicals having 1 to 16 carbon atoms, and aryl radicals having 6 to 15 carbon atoms; a is 0 or 1, and n is an integer from 1 to 6; the reaction being carried out at 150° to 250° C. and 450 to 600 bars.

2. The method of claim 1 wherein the reaction is carried out in the presence of 5 to 25% by weight of water, based on said methanol.

3. The method of claim 1 wherein said iodine or iodide is alkali metal iodide.

4. The method of claim 1 wherein $R_1$ and $R_2$ are joined to each other, and $R_3$ and $R_4$ are joined to each other.

5. The method of any of claims 2, 4, 3 or 1 wherein a first molar ratio of cobalt to methanol is 1:20 to 1:10,000, and a second molar ratio of cobalt to phosphine or phosphite is 1:1 to 1:20.

6. The method of claim 5 wherein said first molar ratio is 1:30 to 1:2000, and said second molar ratio is 1:1 to 1:5.

7. The method of claim 1 wherein the atomic ratio of cobalt to ruthenium is 1:0.0005 to 1:0.5.

8. The method of claim 7 wherein said atomic ratio is 1:0.05 to 1:0.1.

9. The method of claim 1 wherein the molar ratio of cobalt to iodine or iodide is 1:0.02 to 1:2.

10. The method of claim 9 wherein said molar ratio is 1:0.1 to 1:1.

11. The method of claim 1 wherein said bi-dentate phosphine or phosphite is 1,3-bis-(diphenoxyphosphino)-propane or bis-(diphenylphosphino)-methane.

12. The method of claim 1 wherein the reaction is carried out at 160° to 230° C.

13. The method of claim 1 wherein the molar ratio of said hydrogen to said carbon monoxide is 1:1 to 10:1.